US00PP28092P2

(12) United States Plant Patent
Wood

(10) Patent No.: US PP28,092 P2
(45) Date of Patent: Jun. 13, 2017

(54) ***VIBURNUM* PLANT NAMED 'SMVDE'**

(50) Latin Name: *Viburnum dentatum*
Varietal Denomination: SMVDE

(71) Applicant: Timothy Wood, Spring Lake, MI (US)

(72) Inventor: Timothy Wood, Spring Lake, MI (US)

(73) Assignee: Spring Meadow Nursery Inc, Grand Haven, MI (US)

( * ) Notice: Subject to any disclaimer, the term of this patent is extended or adjusted under 35 U.S.C. 154(b) by 0 days.

(21) Appl. No.: 14/998,625

(22) Filed: Jan. 20, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Cassandra Bright

(57) ABSTRACT

A new and distinct *Viburnum* cultivar named 'SMVDE' is disclosed, characterized by a Very strong blooming, dense branching and very glossy foliage. The new variety is a *Viburnum*, normally produced as an outdoor garden or container plant.

2 Drawing Sheets

Latin name of the genus and species: *Viburnum dentatum*.
Variety denomination: 'SMVDE'.

BACKGROUND OF THE INVENTION

The new *Viburnum* cultivar is a product of a planned breeding program conducted by the inventor, Timothy D. Wood, in Grand Haven, Mich. The objective of the breeding program was to produce new *Viburnum* varieties of compact habit better container presence, with new and better foliage types. The open pollination resulting in this new variety was made during Summer of 2007.

The seed parent is an unpatented, unnamed variety *Viburnum dentatum*. The pollen parent is unknown, as it was an open pollination breeding program. The new variety was identified as a potentially interesting selection in 2009, at a commercial greenhouse in Grand Haven, Mich.

Asexual reproduction of the new cultivar 'SMVDE' by softwood cuttings was first performed during the June of 2009, at a commercial greenhouse in Grand Haven, Mich. Subsequent propagation has shown that the unique features of this cultivar are stable and reproduced true to type in 3 successive generations.

SUMMARY OF THE INVENTION

The cultivar 'SMVDE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMVDE' These characteristics in combination distinguish 'SMVDE' as a new and distinct *Viburnum* cultivar:

1. Very strong blooming.
2. Dense branching.
3. Very glossy foliage.

PARENT COMPARISON

Plants of the new cultivar 'SMVDE' are similar to plants of the seed parent unpatented, unnamed variety *Viburnum dentatum*, in most horticultural characteristics, however, plants of the new cultivar 'SMVDE' differ in the following;

1. Glossier foliage.
2. Tight upright habit, whereas the seed parent has a more rounded habit.

Pollen parent unknown as this is product of open pollination.

COMMERCIAL COMPARISON

Plants of the new cultivar 'SMVDE' can be compared to the unpatented commercial variety *Viburnum* 'Emerald Luster'. These varieties are similar in most horticultural characteristics; however 'SMVDE' differs in the following:

1. Glossier foliage.
2. Large, pyramidal habit whereas the comparator has a large upright habit.

BRIEF DESCRIPTION OF THE PHOTOGRAPHS

Figure 1:
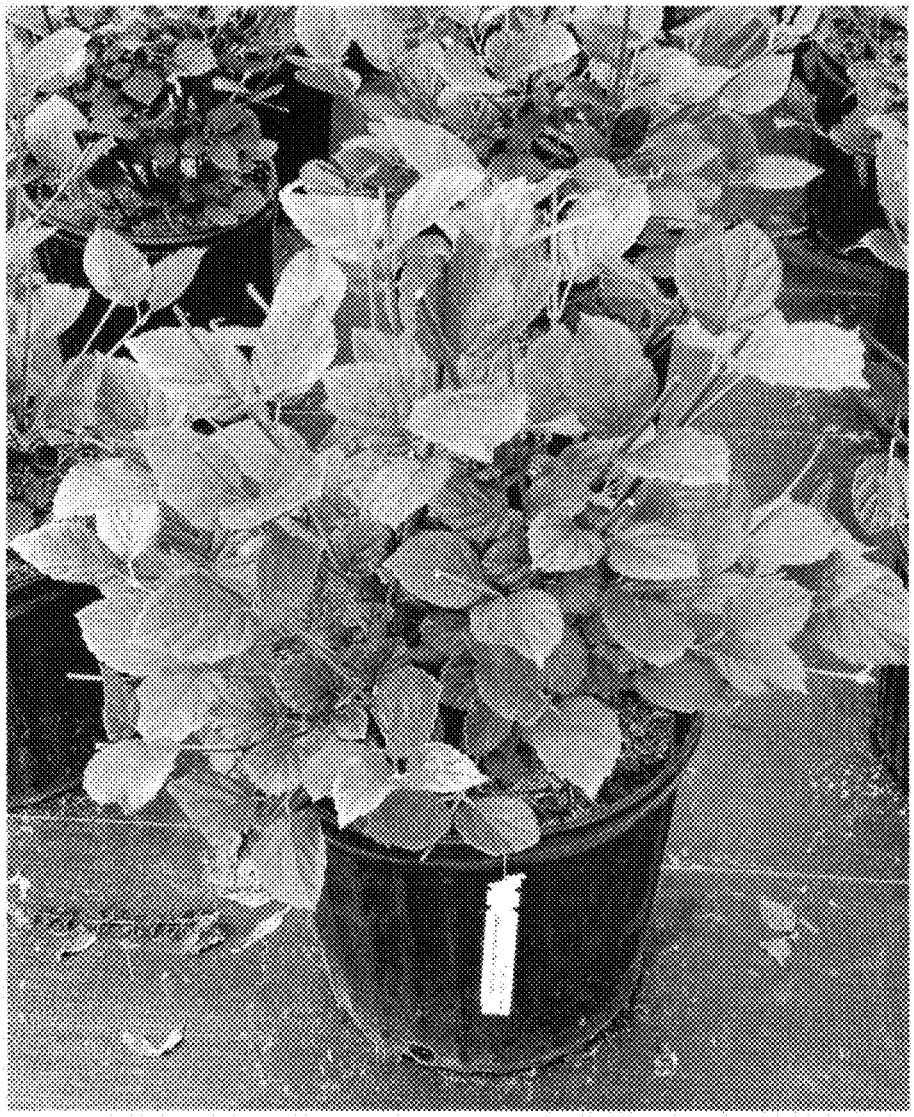

The accompanying photograph in FIG. 1 illustrates in full color a typical plant of 'SMVDE' grown outdoors in a 2 gallon nursery pot, in Grand Haven, Mich. Foliage depicted in FIG. 1 is immature.

Figure 2:
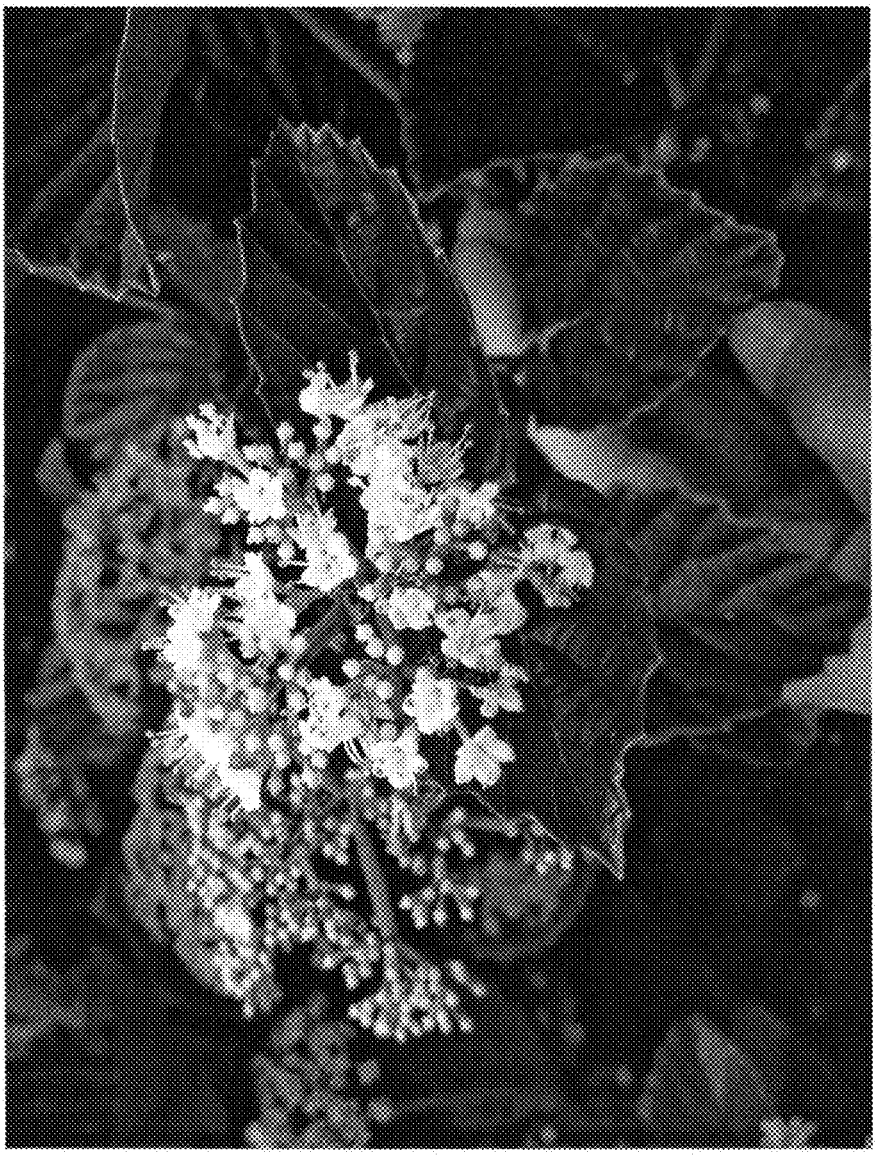

FIG. 2 illustrates in full color a typical inflorescence and mature foliage of 'SMVDE'. Age of the plant photographed is approximately 2 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMVDE' plants grown in a commercial poly greenhouse in Grand Haven, Mich. under natural lighting.

Measurements were taken during Spring of 2015. The plants were 2-3 years old in 2 gallon containers. The growing temperature ranged from 5° C. to 27° C. Measurements and numerical values represent averages of typical plant types. Botanical classification: *Viburnum dentatum* 'SMVDE'.

PROPAGATION

Time to initiate roots: About 30 days at approximately 24° C.

Root description: Dense density freely branching. Root thickness from thick to thin. White to brown in color, not effectively measured with a color chart.

Time to produce a rooted young plant: About 120 days at 24° C.

PLANT

Plant type: Perennial shrub.
Age of plant described: Approximately 2-3 years old.
Growth habit: Upright.
Pot size of plant described: #2 pot.
Overall plant shape: Elliptic.
Height: 75 cm.
Plant spread: 55 cm.
Growth rate: Good.
Plant vigor: Good.
Branching characteristics: Opposite, basal branching. Pinching required.
Length of primary lateral branches: 40 cm.
Diameter of lateral branches: 1 cm.
Quantity of lateral branches: About 5 lateral branches per main branch.
Stem:
- *Stem appearance*.—Round.
- *Stem strength*.—Strong.
- *Stem color*.—Near RHS Yellow-green 144B.
- *Bark*.—Near RHS Grey 201A.
- *Pubescence*.—Slight.
- *Aspect*.—Upright 45°.

Internode length: 5 cm.

FOLIAGE

Leaf:
- *Arrangement*.—Opposite.
- *Leaf shape*.—Ovate.
- *Foliage durability*.—Excellent.
- *Other foliage characteristics*.—Very Glossy.
- *Average length*.—5 cm.
- *Average width*.—5 cm.
- *Apex*.—Acute.
- *Base*.—Cordate.
- *Margin*.—Crenate/dentate.
- *Texture of top surface*.—Smooth, shiny, ruffled along veins.
- *Texture of bottom surface*.—Slightly rough.
- *Color*.—Young foliage upper side: Near RHS Yellow-green 144A. Young foliage under side: Near RHS Yellow-green 144A. Mature foliage upper side: Near RHS Green 137A, but darker. Mature foliage under side: Near RHS Yellow-green 146B.
- *Venation*.—Pattern: Pinnate. Color upper side: Near RHS Yellow-green 146B. Color under side: Near RHS Yellow-green 146D.
- *Petiole*.—Average Length: 1-1.5 cm. Diameter: 3 mm. Petiole color upper side: Near RHS Yellow-green 144C. Petiole color lower side: Near RHS Yellow-green 144C. Petiole Texture upper side: Pubescent. Petiole Texture lower side: Pubescent.

FLOWER

Natural flowering season: Spring to early Summer.
Inflorescence type and habit: Round umbel.
Flower longevity on plant: 2 weeks.
Quantity of flowers per inflorescence: Approximately 300.
Inflorescence size:
- *Width*.—Approximately 6.5 cm.
- *Height*.—Approximately 4 cm.

Quantity of flowers per plant: Thousands of minute flowers per plant.
Individual flowers:
- *Flower form*.—Rotate, whorled.
- *Flower aspect*.—Upright and slightly outward.
- *Flowering habit*.—Terminal ends.
- *Size*.—Diameter: Approximately 5 mm. Depth: Approximately 4 mm. Flower tube diameter: 1 mm. Flower tube length: 2 mm.

Flower other characteristics:
- *Persistence*.—Self cleaning.
- *Fragrance*.—Earthy, musty, pungent.

Petal:
- *Petal arrangement*.—Whorled.
- *Number of petals per flower*.—5.
- *Petal shape*.—Elliptic.
- *Petal base*.—Obtuse.
- *Margin*.—Entire.
- *Tip shape*.—Obtuse.
- *Length*.—2 mm.
- *Width*.—1 mm.
- *Texture*.—Upper: Smooth, silky. Lower: Smooth, silky. Tube: Smooth.

Petal Color:
- *When opening*.—Upper surface: Near RHS White 155A. Lower surface: Near RHS White 155A.
- *Fully opened*.—Upper surface: Near RHS Yellow 2D. Lower surface: Near RHS Yellow 2D. Veins upper and lower: Near RHS Yellow 2D.

Bud:
- *Shape*.—Obovate.
- *Length*.—Approximately 3 mm.
- *Diameter*.—Approximately 2 mm.
- *Color*.—Near RHS Green-white 157C.

Sepals: None.
Peduncle:
- *Length*.—1.5 cm.
- *Diameter*.—2 mm.
- *Color*.—Near RHS Yellow-Green 144A.
- *Orientation*.—Approximately 90°.
- *Strength*.—Good.
- *Texture*.—Semi pubescent.

Pedicel:
- *Length*.—5 mm.
- *Diameter*.—1 mm.
- *Color*.—Near RHS Yellow-Green 144B.
- *Strength*.—Good.
- *Texture*.—Smooth and very slightly pubescent.

REPRODUCTIVE ORGANS

Stamens:

*Number.*—4 to 5.

*Filament length.*—3 mm.

*Filament color.*—Near RHS White 155A.

Anthers:

*Shape.*—Club-like.

*Length.*—1 mm.

*Color.*—Near RHS Greyed-orange 165A.

*Pollen color.*—Near RHS Greyed-orange 165A.

*Pollen amount.*—Moderate.

Pistil:

*Number.*—1.

*Length.*—Less than 1 mm.

*Style.*—Length: Less than 1 mm. Color: Near RHS White 155A.

*Stigma.*—Color: Near RHS White 155A.

OTHER CHARACTERISTICS

Seeds and fruits: Not observed to date.

Disease/pest resistance: Neither resistance nor susceptibility to normal diseases and pests of *Viburnum* have been observed.

Temperature tolerance: The new variety tolerates temperatures between −31° C. to 38° C.

What is claimed is:

1. A new and distinct cultivar of *Viburnum* plant named 'SMVDE' as herein illustrated and described.

* * * * *